United States Patent
Visinoni et al.

(10) Patent No.: US 9,955,953 B2
(45) Date of Patent: May 1, 2018

(54) CONTAINER AND METHOD FOR COLLECTING, TRANSPORTING AND STORING BIOLOGICAL TISSUE SAMPLES

(71) Applicant: Milestone Technologies S.r.l., Torre Boldone (BG) (IT)

(72) Inventors: Francesco Visinoni, Mozzo (IT); Marco Bellini, Bergamo (IT); Giovanni Bussolati, Turin (IT); Michele Martinelli, Brembate (IT)

(73) Assignee: Milestone S.r.l., Sorisole (BG) (IT)

( * ) Notice: Subject to any disclaimer, the term of this patent is extended or adjusted under 35 U.S.C. 154(b) by 305 days.

(21) Appl. No.: 14/686,803

(22) Filed: Apr. 15, 2015

(65) Prior Publication Data

US 2016/0157837 A1   Jun. 9, 2016

(30) Foreign Application Priority Data

Dec. 8, 2014   (EP) ..................... 14196823

(51) Int. Cl.
*A61B 10/00*   (2006.01)
*G01N 1/30*   (2006.01)
*B01L 3/00*   (2006.01)

(52) U.S. Cl.
CPC ............ *A61B 10/0096* (2013.01); *B01L 3/50* (2013.01); *B01L 3/502* (2013.01); *G01N 1/30* (2013.01); *B01L 2200/0673* (2013.01); *B01L 2200/142* (2013.01); *B01L 2200/16* (2013.01); *B01L 2300/028* (2013.01); *B01L 2300/042* (2013.01); *B01L 2300/0832* (2013.01); *B01L 2300/0851* (2013.01); *B01L 2400/0677* (2013.01); *G01N 2001/305* (2013.01)

(58) Field of Classification Search
CPC .... C12Q 2527/125; C07C 45/86; C12N 1/04; G01N 1/30; Y10T 436/25; C08L 61/02; B01L 2200/142
See application file for complete search history.

(56) References Cited

U.S. PATENT DOCUMENTS

2006/0199735 A1 *   9/2006   Hamley ................... A01N 3/00
                                                             504/114
2012/0270293 A1 * 10/2012   Chu ..................... A01N 1/0284
                                                             435/173.5

FOREIGN PATENT DOCUMENTS

WO   WO-2013192607 A1 * 12/2013 ............... G01N 1/36

* cited by examiner

*Primary Examiner* — Lynn Y Fan
(74) *Attorney, Agent, or Firm* — The H.T. Than Law Group

(57) ABSTRACT

The invention refers to a container (1) for collecting, transporting and storing biological tissue samples, wherein the container (1) is filled with a first component (3) being a fixative and a second component (4) being a fluid, wherein the second component (3) has a lower specific gravity compared to the fixative (3), and is immiscible with the fixative (3). The second component (4) is stratified on top of the fixative (3) to form a protective film to prevent fixative fumes to escape from the container (1). The invention further relates to a method for collecting, transporting and storing biological tissue samples. The method comprises the steps of: filling a first component (3) being a fixative in a container (1), and filling a second component (4) being a fluid in the container (1) filled with the first component (3), wherein the second component (4) has a lower specific gravity compared to the fixative (3) and is immiscible with the fixative (3) so that the second component (4) is stratified on top of the fixative (3) to form a protective film to prevent fixative fumes to escape from the container (1). The method further comprises the step of placing a biological tissue sample into the first component (3) before or after the second component (4) has been filled into the container (1).

19 Claims, 1 Drawing Sheet

Figure 2:
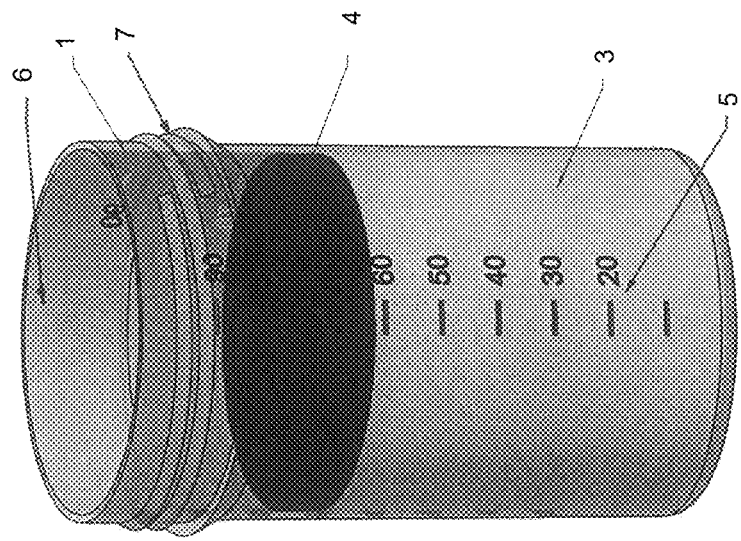

CONTAINER AND METHOD FOR COLLECTING, TRANSPORTING AND STORING BIOLOGICAL TISSUE SAMPLES

The present invention relates to a container as well as a method for collecting, transporting and storing biological tissue samples, wherein the container is filled with a fixative.

In the fields of histology, pathology and cell biology, fixation is a critical step in the preparation of histological sections by which biological tissues are preserved from decay, thereby preventing autolysis or putrefaction. The structure of a tissue is determined by the shapes and sizes of macromolecules in and around cells. The principal macromolecules inside a cell are proteins and nucleic acids. Fixation terminates any ongoing biochemical reactions, and it may also increase the mechanical strength or stability of the treated tissues. The broad objective of tissue fixation is to preserve cells and tissue components and to do this in such a way as to allow for the preparation also of thin, stained sections.

By far the most commonly used fixative in histology is formaldehyde, an organic compound with the formula $CH_2O$ or HCHO. It is the simplest aldehyde and it is also known by its systematic name methanal. The common name of this substance comes from its similarity and relation to formic acid.

It is usually used as a 10% Neutral Buffered Formalin (NBF), that is approximately 3.7% to 4.0% formaldehyde in phosphate buffered saline. Because formaldehyde is a gas at room temperature, formalin-formaldehyde gas dissolved in water is used when making the former fixative. Formaldehyde fixes tissues by cross-linking the proteins, primarily the residues of the basic amino acid lysine.

Considering that formaldehyde is widely used in several industrial processes and consumers' products, the International Agency for Research on Cancer (IARC), part of the WHO (World Health Organization), has evaluated the carcinogenicity of formaldehyde several times. In 2006, IARC concluded that formaldehyde is a known carcinogen on human (group 1) on the basis of induction of nasopharyngeal cancers (Monographs on the Evaluation of the Carcinogenic Risk of Chemicals to Man).

A large amount of relevant publications on both animals and humans on toxicity, carcinogenicity and mutagenicity of formaldehyde has been published in the past 20 years.

Several reviews of the toxicological properties of formaldehyde have also been published by international and national organizations, including the American NCI (National Cancer Institute).

In Europe the safety correlated to the wide use of formaldehyde resulted in a reclassification of this substance. When evaluating the carcinogenicity of substances, European Union (EU) regulators took into account evidence from studies on both animals and humans. Since 1980 over hundred studies have been undertaken investigating the potential correlation between formaldehyde and cancer.

On December 2013 the EU-REACH (Registration, Evaluation, Authorization and Restriction of Chemicals) adopted a decision to reclassify formaldehyde as a Category 1B carcinogen and Category 2 mutagen under the EU CLP (Classification, Labelling and Packaging) Regulation.

As a Category 1 carcinogen, formaldehyde use will be regulated by the restrictive Carcinogens Directive in EU workplaces. This will mandate the replacement of formaldehyde with less dangerous alternatives and, when that is not possible, restricting exposure using engineering and other controls. Personal Protective Equipment alone will not be considered adequate measure for controlling exposure to carcinogens. Mandatory prevention and protection obligations are:

Eliminate the substance or replace it with a substance which is not or less dangerous.

If substitution is not technically feasible because the substance is unique and irreplaceable, use a closed system to comply with existing occupational exposure limit values.

Minimize the number of workers exposed, the workers exposure and reduce level of exposure as much as possible; constantly monitor the workers' health.

These new classifications of formaldehyde will impact on routine histopathological examinations performed on all biological samples including core biopsies, endoscopic biopsies, small and large surgical resection specimens and bone marrow biopsies, because all specimens for routine histological examination are generally collected into containers with 10% neutral-buffered formalin (NBF) solution.

Generally, the containers used for collecting histological samples vary from a volume of 10 ml to a volume of 10 liters. Either empty containers to be filled with NBF at the time of the specimen collection by the operator at the surgical room or at the histology laboratory, or already prefilled containers with NBF are commercially available. Both methods expose operators to formalin fumes during the sample collection, as these procedures are normally carried out in open space not vented environment. The exposure to formaldehyde by the operator happens during the container opening and during the specimen handling (e.g. placement) as this procedure normally takes from several seconds to minutes dependent on the type and dimension of the specimen. A larger specimen is generally placed in the container by hand, while a smaller specimen is handled by using surgical forceps. In addition, the small biopsies (i.e. endoscopic, bone marrow or core needle) are directly placed in the fixative container by using the tool used for the collection from the patient. The use of prefilled containers reduces the length of exposure compared to containers that need to be filled during the specimen collection, but does not completely eliminate the safety risk for the operator.

In the past twenty years many commercial companies offered to the market alternative fixatives to formalin, but as of today, several studies and researches provided that NBF still remains the preferred and irreplaceable type of fixative for histological examination.

It is thus an object of the present invention to provide a suitable container and method for collecting, transporting and storing histological samples in a fixative like NBF with which a severe reduction or even elimination of the (toxic) fume exposure to the operator can be achieved.

This object is achieved by the subject-matter of the independent claims. The dependent claims study further the central idea of the present invention.

According to a first aspect, the present invention relates to a container for collecting, transporting and storing biological tissue samples. The container is filled with a first component being a (fluid or liquid) fixative. The fixative can be a solution. According to a preferred embodiment, this fixative is formalin, preferably 10% neutral buffered formalin (NBF), zinc-formalin or glutaraldehyde or any other fixative used in histology. The container is further filled with a second component being a fluid and having a lower specific gravity compared to the first component (i.e. the fixative) and also being immiscible with the first component. The second component can be a liquid, a jelly, a gel, a foam or the like. The second component can be a solution, preferably a single solution or a blended solution of organic or inorganic components. Moreover, the second component is preferably less toxic than the fixative and more preferably has no or just a low toxicity for human beings by inhalation. According to a preferred embodiment, the second component can be made by mineral oils or a mixture of mineral oils, hydrocarbons or a mixture of hydrocarbons, or by isoparaffin C9-C12. The second component is preferably in a liquid, jelly or foamy state/form. Further, the second component may contain a dye to better distinguish the second component from the fixative. According to a preferred embodiment of the invention, the volume of the second component is from 0.1% to 50% of the total volume of both the first and second components, more preferably between 3% to 5%.

According to the invention, the second component is stratified (i.e. layered) on top of the fixative to form a protective film to prevent fixative fumes to escape from the container. In other words, the first component forms a lower layer being provided in the container while the second component forms a top layer being provided on top of the lower layer (i.e. the first component) and preferably in plane contact with the top surface of the first component in the container. To allow a secure protection of escaping fumes of the fixative, the second component preferably completely covers the top surface of the first component in the container. Due to its material properties and fluid (i.e. flowable) characteristics, the second component spreads over the top surface of the first component once being applied (i.e. poured into the container and onto the first component) to completely cover upper surface of the first component thus forming a corresponding protective film preventing the escape of fixative fumes. The container can preferably have a volume of between 5 ml and 10000 ml (i.e. 10 liters). According to a preferred embodiment, the container can further comprise a lid member for selectively closing (and opening) a top opening of the container.

According to the present invention, a "fluid" is to be understood as a flowable component/medium (e.g. a liquid, a jelly, a gel, a foam, a solution, a medium having a more or less high/low viscosity, etc.) which fulfills the requirements according to the present invention; i.e. it must have a lower specific gravity compared to the used first component, it must be immiscible with the used first component and it must be stratifiable (i.e. layerable) on top of the first component (e.g. by being poured into the container and onto the fixative) to stay there above/on top of the first component once being applied (e.g. filled or poured) on the first component to form a corresponding protective film.

According to a second aspect, the present invention relates to a method for collecting, transporting and storing biological tissue samples. The method comprises a first step of filling (e.g. pouring or discharging) a first component being a fixative in a container for collecting, transporting and storing the biological tissue samples. According to a second step of the method, a second component being a fluid is filled (e.g. poured or discharged) in the container (pre-)filled with the first component. The second component has a lower specific gravity compared to the fixative and is immiscible with the fixative so that the second component is stratified on top of the first component to form a protective film to prevent fixative fumes to escape from the container. According to a further step of the method, a biological tissue sample is placed into the first component which has been filled into the container—preferably in a manner to completely store and submerge the sample only in the first component—before or after the second component has been filled into the container.

According to an embodiment of the present invention, the biological tissue sample can preferably be directly placed in the first component which has already been (pre-)filled into the container or—alternatively—it can be placed in a histological cassette before being placed in the first component (i.e. fixative) together with the histological cassette carrying the biological tissue sample. However, in the majority of the cases the biological tissue is placed directly (i.e. free) in the fixative in the container (e.g. transportation vial). The histological cassette is only used in some limited cases (e.g. in case the samples need a special orientation; for example prostate needle biopsies) as an alternative to the direct placement of the specimen in the fixative.

A lid member can preferably be placed, more preferably removably placed, on a container opening of the container to close the container. Even if the filling and/or placing steps are usually carried out manually, at least one, more or all of the filling and/or placing steps can be carried out semi-automatically or automatically instead of being carried out manually. However, the invention is not limited to a particular type of action for carrying out the respective method steps.

To summarize, the invention consists in (plastic) containers being (pre-)filled with a fixative like standard NBF used routinely in histology. In alternative to NBF, other fixatives used in histology can also be used according to the invention, such as zinc-formalin or glutaraldehyde. To minimize the workflow impact and commercial costs of this new container and method, the containers according to this invention can be similar in shape, design, dimensions and composite material to the common containers currently used in histology.

In addition to NBF or any other alternative fixative, the container is also partially filled with a (small) quantity of an additional fluid component (e.g. a chemical solution) that, thanks to its composition, is immiscible (e.g. hydrophobic) with the used fixative like NBF. This second component has a lower specific gravity (or lower density or lower specific weight) than the first component placed in the container. The result of this dual component (e.g. chemical solutions) filled in the container is a stratification of the two substances forming two layers extending over the overall cross-sectional area of the container with the fixative layer being at the bottom and the second fluid component layer being on top of the first component, preferably in direct (and plane) contact with its upper surface.

The second component being stratified on the top of the first component thus forms a sort of protective film to prevent fixative (i.e. formalin) fumes to escape when the container is open; e.g. when the container's lid member is opened.

The second component can be made by a chemical mixture of oils or aromatic substances able to remain separate from the fixative (preferably NBF) to prevent interferences with the correct formalin fixation procedure that occurs to the histological specimen placed into the container.

As already mentioned before, such kind of second component could be, for example, made from organic or inorganic compositions having zero or low level of toxicity. An example of an inorganic composition with low level of toxicity can be, for instance, isoparaffin. Isoparaffin is a mixture of hydrocarbons (mineral oils) derived from petroleum and are already used in histology sample preparation as lipids solvents.

In particular, a solvent like isoparaffin C9-C12 has the characteristics described above, i.e. being lighter than the fixative like NBF (i.e. having a lower specific gravity/lower density/lower specific weight) and also being immiscible with the used fixative (i.e. hydrophobic), with the advantage of being non-toxic for the operator by inhalation.

The proportion between the fixative and the second component can be dependent on the maximum volume of the container used and should be suitable to completely store and submerge the sample only in the fixative.

The histological sample can be placed directly into the container being (pre-)filled with the first component (by hand, forceps or needle used by the surgeon, physician or nurse to collect the specimen from the patient) or into histological cassettes, in case the samples need a special orientation (e.g. prostate needle biopsies).

Once the specimen (directly or being placed in a histological cassette) is placed into the container, the second component quickly reforms the protective film by its aggregation on top of the fixative. This results in a total elimination of formalin fumes exposure to the operator.

In this regard, it is noted that both the first and the second component are preferably filled into the container before the biological tissue samples are placed in the first component. For particular applications or in case the samples must not get into contact with a second component, the second component can also be filled into the container after the biological tissue samples have been placed into the first component being (pre-)filled in the container. The filling of the first and second components into the container as well as the placement of the biological tissue samples into the container can be carried out manually, (partially) semi-automatic or (partially) automatic.

Figure 1:
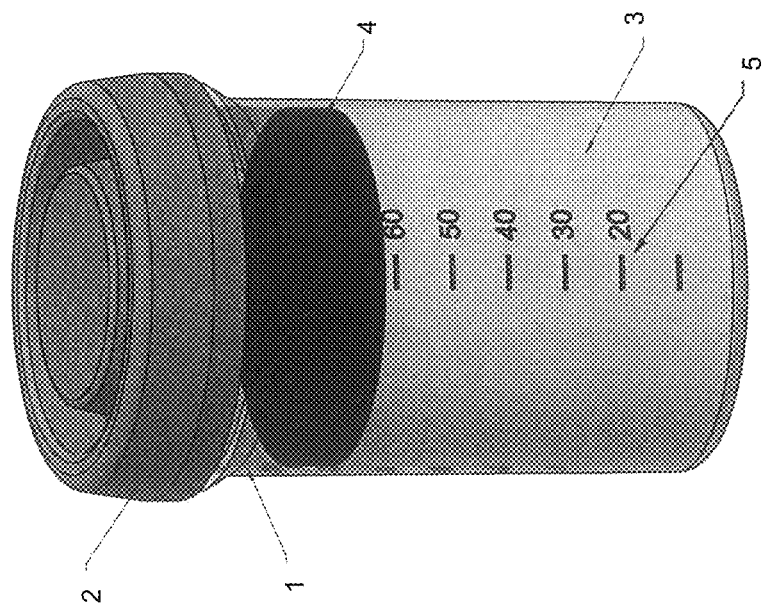

Further advantages and specific features will now be described with respect to the accompanied figures, according to which:

FIG. 1 is a perspective view of a container according to the present invention in a closed state, and FIG. 2 is a perspective view of the container according to FIG. 1 in an opened state.

FIGS. 1 and 2 both show a container 1 for collecting, transporting and storing biological tissue samples according to the present invention. The container 1 can be similar or identical in shape, design, dimensions and composite material to containers commonly used in histology. The container 1 can thus be made, for instance, of a plastic material but the present invention is not limited to such a material. The container 1 preferably has only one opening 6 which is a top opening and which is used for filling the container 1 with the components 3, 4 as well as placing and removing biological tissue samples to be collected, transported and stored (in the fixative 3 filled) in the container 1. The container 1 can preferably have a volume of between 5 ml and 10 l while the present invention is also not limited to this volume which can also be lower or higher according to the particular need and samples (e.g. sample size, type of sample, etc.) to be treated. In a preferred embodiment, the container 1 is made from a transparent material so that the filling level and the position of the biological tissue sample can be identified by the operator from an outside of the container 1. Preferably, a (printed) scale 5 can be provided on the container 1 to allow for a determination and quantification of the filling level of the respective components 3, 4 to be filled into the container 1 even without the additional use of a weighing machine.

As can be seen in FIG. 1, the container 1 can be provided with a lid member 2 for selectively closing and opening the container 1, i.e. selectively closing and opening the top opening 6 of the container 1. For securely fixing the lid member 2 on the container 1, a corresponding fixing means 7 can be provided on the container 1 and/or the lid member 2. The fixing means 7 can be, for instance, a screw joint or bayonet joint provided by a corresponding profiled surface of the matching surfaces of the container 1 on the one hand and the lid member 2 on the other hand. For a tight closure of the container 1, a sealing member (e.g. a sealing gasket) can be provided between the container 1 and the lid member 2 in a closed state of the container 1. The sealing member can be provided on the container 1 and/or in the lid member 2. It is also possible that the fixing means can be configured by the lid member 2 itself being press-fitted onto the container 1; the press-fitting can be further supported by a corresponding sealing member allowing for a tight press-fit connection.

According to the invention, the container 1 is (pre-)filled with two components. The first component 3 is a fixative, particularly a histological fixative. Usually, the fixative can be formaldehyde which is commonly used in histology as 10% neutral buffered formalin (NBF; that is approx. 3.7% to 4.0% formaldehyde in phosphate buffered saline). The fixative 3 can also be a zinc-formalin or glutaraldehyde or any other suitable fixative for histology. Usually, these fixatives 3 are toxic and are used for preserving the biological tissue sample being placed therein.

The second component 4 is usually filled into the container 1 after the container 1 has been (pre-) filled with the first component 3. The second component 4 is a fluid (e.g. a liquid or liquid solution). The second component 4 has a lower specific gravity (or density or specific weight) compared to the first component 3. Moreover, the second component 4 is immiscible with the first component 3. It is thus possible to stratify the second component 4 on top of the first component 3 so that the second component 4 covers the whole top surface of the first component 3. These two layered components 3, 4 are thus provided in the container 1 such that the first component 3 is at a bottom of the container 1 (preferably opposite the top opening 6) and the second component 4 is placed (preferably in direct and plane contact with the first component 3) on top of the first component 3. Thereby, the second component 4 can form a protective film on top of the first component 3 within the container 1 to prevent fumes of the first component 3 to escape from the container 1. It is thus possible to eliminate or at least severely reduce the fume exposure of the operators involved in the specimens collection and examination.

Just as an example, the first component 3 can be associated to water, e.g. being the NBF basically comprising 4% formaldehyde and 96% water. In this exemplary case, the specific gravity is around 1. In this case, a second component is used having a specific gravity of about between 0.79 to 0.93. However, the present invention is not limited to this example.

The volume of the second component 4 is preferably from 0.1% to 50% of the total volume of both components (i.e. first component 3+second component 4) and is more preferable between 3% to 5%. It is thus possible to provide a sufficiently thick and thus secure protective film on top of the first component 3.

The second component 4 can be a solution, preferably a single solution or a blended solution of organic or inorganic components. The second component 4 is preferably less toxic than the fixative and more preferable has no or low toxicity for human beings by inhalation. According to a preferred embodiment, the second component 4 can be made by mineral oils or a mixture of mineral oils, hydrocarbons or a mixture of hydrocarbons, or by isoparaffin C9-C12. As an example, the occupational Exposure Limit Values (TLV-TWA) of Isoparaffin hydrocarbons C9-C12 is an average of 300 ppm, while formalin is an average of 0.75 ppm for an eight hour work day. When considering a short-term exposure limit (TLV-STEL), which is the maximum exposure allowed during a 15 minute period, for formalin it is 2 ppm, while for Isoparaffin C9-C12 it is not even reported in the reagent Material Safety Data Sheets (MSDS) as it is irrelevant. The second component 4 can be, for instance, provided in a liquid, jelly or foamy state. According to a preferred embodiment, the second component 4 can contain a dye to better distinguish the second component 4 from the first component 3 when being filled in the container 1 and layered one above the other.

The present invention thus consists in a (pre-)filled container 1 for collecting, transporting and storing biological specimens for histological examination. The container 1 is (pre-)filled with two components, wherein the first component 3 is a suitable histological fixative and the second component 4 is a fluid—preferably an organic or inorganic solution—having lower specific gravity compared to the first component 3 and being immiscible with the fixative 3. By means of the second component 4, a protective film can be created on top of the first component to prevent its fumes to escape when the container 1 is open; e.g. in case the lid member 2 is opened for placing the sample into or removing the sample out of the container 1. The present invention thus makes it possible to continue the use of preferred and still irreplaceable types of toxic fixatives such as formaldehyde due to the severe reduction or even elimination of the fume exposure of operators involved in the specimens collection and examination.

In the following, a preferred method for collecting, transporting and storing biological tissue samples is described.

In a first step of the method, a first component 3 is filled (e.g. poured or discharged) in the container 1. The first component 3 is a fixative as already described herein above.

In a second step of the method, a second component 4 is filled (e.g. poured or discharged) in the container 1. The second component 4 is a fluid and has a lower specific gravity compared to the first component 3 and is also immiscible with the first component 3. Hence, the second component 4 can be easily stratified on top of the first component 3 to form a protective film on or over the top surface of the first component 3 to prevent fixative fumes to escape from the container 1. In other words, the two components 3, 4 filled in the container 1 are provided in the container 1 in a layered manner, wherein the first component 3 is provided as a bottom layer and the second component 4 is provided as a top layer completely covering the top surface of the first component 3 so that the first component 3 is not exposed to the container opening 6. Due to its material properties and fluid (i.e. flowable) characteristics, the second component 4 spreads over the whole top surface of the first component 3 once being filled into the container 1 and onto the first component 3 to thus completely cover the upper surface of the first component 3 thus forming the mentioned protective film for preventing the escape of fixative fumes.

The method according to the present invention further comprises the step of placing a biological tissue sample into the first component 3 before or even after the second component 4 has been filled into the container 1. In a preferred embodiment, the container 1 has been pre-filled with both the first component 3 and the second component 4 before the biological tissue sample is placed into the container 1, particularly into the first component 3 in the container 1. In this regard, it is again noted that the proportion between the first component 3 and the second component 4 should be suitable to completely store and submerge the sample only in the first component 3.

Before the biological tissue sample is placed into the first component 3, the biological tissue sample can also be placed in a histological cassette which is then placed together with the biological tissue sample into the first component 3.

Moreover, the lid member 2 can be (removably) placed on the container 1—preferably after having filled both components 3, 4 into the container and having placed the biological tissue sample into the container 1—to close the container 1, i.e. a (top) opening 6 of the container 1.

At least one, some or even all of the filling and/or placing steps described before can be carried out (partially) semi-automatic or (partially) automatic. It is, however, also possible that at least some or all of the method steps are carried out manually.

It is needless to say that as a final step, the biological tissue sample can again be removed from, i.e., out of the container 1.

The present invention is not limited to the embodiment as described herein above. All the features in the embodiments can be interchangeably combined as long as being covered by the appended claims. In particular, the present invention is not limited to the type of the first component 3 as long as it is suitable for collecting, transporting and storing a biological tissue sample, i.e. as long as it is a suitable fixative. Moreover, the invention is also not limited to the second fluid component 4 as long as it fulfills the requirements of having a lower specific gravity compared to the first component 3 and being immiscible with the first component 3 to thus form a protective film on top of the first component 3 avoiding fixative fumes from escaping from the container 1. Moreover, the invention is also not limited to the shape, design, dimensions and composite materials of the container 1 and lid member 2 as long as they are suitable for the corresponding field of histology and thus also for storing the corresponding components 3, 4 and biological tissue samples even for a long time.

The invention claimed is:

1. Container (1) for collecting, transporting and storing biological tissue samples comprising a first component (3) and a second component (4), wherein the container (1) is filled with the first component (3) being a fixative and the second component (4) being a fluid, wherein the second component (4)
   has a lower specific gravity compared to the fixative (3), and
   is immiscible with the fixative (3), and
   wherein the second component (4) is stratified on top of the fixative (3), such that the second component completely covers the top surface of the first component in the container to form a protective film to prevent fixative fumes to escape from the container (1).

2. Container (1) according to claim 1, wherein the second component (4) is a solution.

3. Container (1) according to claim 1, wherein the second component (4) is less toxic than the fixative (3).

4. Container (1) according to claim 1, wherein the second component (4) is made by mineral oils or a mixture of mineral oils, hydrocarbons or a mixture of hydrocarbons, or by Isoparaffin C9-C12.

5. Container (1) according to claim 1, wherein the second component (4) is in a liquid, jelly or foamy state.

6. Container (1) according to claim 1, wherein the second component (4) contains a dye to better distinguish the second component (4) from the fixative (3).

7. Container (1) according to claim 1, wherein the first component (3) is a solution.

8. Container (1) according to claim 1, wherein the first component (3) is formalin.

9. Container (1) according to claim 1, wherein the volume of the second component (4) is from 0.1% to 50% of the total volume of both components (3, 4).

10. Container (1) according to claim 1, wherein the container volume is between 5 ml and 10 l.

11. Container (1) according to claim 1, further comprising a lid member (2) for selectively closing a top opening (6) of the container (1).

12. Method for collecting, transporting and storing biological tissue samples within a container (1) according to claim 1, comprising the steps of:

filling the first component (3) in the container (1), filling the second component (4) in the container (1) filled with the first component (3), the method further comprising the step of placing a biological tissue sample into the first component (3) before or after the second component (4) has been filled into the container (1).

13. Method according to claim 12, wherein the biological tissue sample is directly placed in the first component (3) which has been filled into the container (1) or is placed in a histological cassette before being placed in the first component (3) together with the histological cassette carrying the biological tissue sample.

14. Method according to claim 12, wherein a lid member (2) is placed, preferably removably placed on a container opening (6) of the container (1) to close the container (1).

15. Method according to claim 12, wherein the filling and/or placing steps are carried out manually or at least one of the filling and/or placing steps is carried out semi-automatically or automatically.

16. Container (1) according to claim 2, wherein the solution is a single solution or a blended solution of organic or inorganic components.

17. Container (1) according to claim 3, wherein the second component (4) has no or low toxicity for human beings by inhalation.

18. Container (1) according to claim 8, wherein the first component (3) is 10% neutral buffered formalin (NBF), zinc-formalin or glutaraldehyde.

19. Container (1) according to claim 9, wherein the volume of the second component (4) is from 3% to 5% of the total volume of both components (3, 4).

* * * * *